(12) United States Patent
Alfery et al.

(10) Patent No.: US 7,013,899 B2
(45) Date of Patent: Mar. 21, 2006

(54) PERILARYNGEAL ORAL AIRWAY WITH MULTI-LUMEN ESOPHOGEAL-OBTURATOR

(75) Inventors: David D. Alfery, Nashville, TN (US); Brad Quinn, Indianapolis, IN (US)

(73) Assignee: Engineered Medical System, Inc., Indianapolis, IN (US)

( * ) Notice: Subject to any disclaimer, the term of this patent is extended or adjusted under 35 U.S.C. 154(b) by 0 days.

(21) Appl. No.: 10/917,600

(22) Filed: Aug. 13, 2004

(65) Prior Publication Data

US 2006/0032505 A1 Feb. 16, 2006

(51) Int. Cl.
*A61M 16/00* (2006.01)
(52) U.S. Cl. .............................. 128/207.18; 128/200.26
(58) Field of Classification Search ........... 128/200.24, 128/200.26, 207.14, 207.15, 201.26, 206.24, 128/911, 912, DIG. 26, 207.16, 207.29, 207.18; 604/96.11, 8, 9, 35, 96.01
See application file for complete search history.

(56) References Cited

U.S. PATENT DOCUMENTS

| | | | |
|---|---|---|---|
| 2,220,493 A | 11/1940 | Pixler | |
| 3,421,510 A | 1/1969 | Kettenbach | |
| 3,756,244 A | 9/1973 | Kinnear | |
| 3,774,616 A | 11/1973 | White | |
| 3,908,665 A | 9/1975 | Moses | |
| 4,046,139 A | 9/1977 | Horn | |
| 4,054,135 A | 10/1977 | Berman | |
| 4,063,561 A | 12/1977 | McKenna | |
| 4,067,331 A | 1/1978 | Berman | |
| 4,091,816 A | 5/1978 | Elam | |
| 4,158,916 A | 6/1979 | Adler | |
| 4,230,108 A | 10/1980 | Young | |
| 4,256,099 A | 3/1981 | Dryden | |
| 4,263,921 A | 4/1981 | Trugillo | |
| 4,265,621 A | 5/1981 | McVey | |
| D261,442 S | 10/1981 | Anderson | |
| 4,321,921 A | 3/1982 | Laszczower | |
| 4,328,056 A | 5/1982 | Snooks | |
| 4,338,930 A | 7/1982 | Williams | |
| 4,383,534 A | 5/1983 | Peters | |
| 4,454,887 A | 6/1984 | Kruger | |
| 4,497,318 A | 2/1985 | Donmichael | |
| 4,497,324 A | 2/1985 | Sullivan | |

(Continued)

FOREIGN PATENT DOCUMENTS

EP 0 665 029 A2 8/1995

(Continued)

*Primary Examiner*—Teena Mitchell
(74) *Attorney, Agent, or Firm*—Swanson & Bratschun LLC

(57) ABSTRACT

A tubular assembly having a plurality of lumens is configured for insertion into the mouth and throat of a patient with a proximal end of the tubular assembly extending from the patient's mouth and a distal end of the tubular assembly extending into the patient's esophagus. The tubular assembly further includes a transition portion near the tubular assembly. The transition portion is configured to transition from a relatively radially large proximal end to a relatively radially small distal end, with the relatively radially small distal end being in communication with at least one of the lumens. The relatively radially large proximal end is configured to abut the aryepiglottic folds of the patient to arrest insertion of the tubular assembly with the relatively radially small distal end of the transition portion extending into the patient's esophagus. A method of providing breathing assist includes inserting the tubular assembly into the mouth and throat of a patient with the relatively radially large proximal end abutting the aryepiglottic folds and the distal end of the transition portion extending into the patient's esophagus.

19 Claims, 5 Drawing Sheets

U.S. PATENT DOCUMENTS

| | | |
|---|---|---|
| 4,502,482 A | 3/1985 | DeLuccia |
| 4,509,514 A | 4/1985 | Brain |
| 4,509,519 A | 4/1985 | Detsch |
| 4,527,553 A | 7/1985 | Upsher |
| 4,584,998 A | 4/1986 | McGrail |
| 4,612,927 A | 9/1986 | Kruger |
| 4,674,495 A | 6/1987 | Orr |
| 4,683,879 A | 8/1987 | Williams |
| 4,685,447 A | 8/1987 | Iversen. |
| 4,688,568 A | 8/1987 | Frass |
| 4,759,356 A | 7/1988 | Muir |
| 4,796,640 A | 1/1989 | Webler |
| 4,825,858 A | 5/1989 | Frankel |
| 4,827,910 A | 5/1989 | Mathews, III |
| 4,832,020 A | 5/1989 | Augustine |
| 4,848,331 A | 7/1989 | Northway-Meyer |
| 4,852,565 A | 8/1989 | Eisele |
| 4,919,126 A | 4/1990 | Baildon |
| 4,976,261 A | 12/1990 | Gluck |
| 5,038,766 A | 8/1991 | Parker |
| 5,057,106 A | 10/1991 | Kasevich |
| 5,163,423 A | 11/1992 | Suzuki |
| 5,174,283 A | 12/1992 | Parker |
| 5,176,692 A | 1/1993 | Wilk |
| 5,203,320 A | 4/1993 | Augustine |
| 5,295,489 A | 3/1994 | Bell |
| 5,303,697 A | 4/1994 | Brain |
| 5,309,906 A | 5/1994 | LaBombard |
| 5,323,771 A | 6/1994 | Fisher |
| 5,339,805 A | 8/1994 | Parker |
| 5,356,391 A | 10/1994 | Stewart |
| 5,357,954 A | 10/1994 | Shigezawa |
| 5,365,940 A | 11/1994 | Teves |
| 5,372,131 A | 12/1994 | Heinen, Jr. |
| 5,392,774 A | 2/1995 | Sato |
| 5,443,063 A | 8/1995 | Greenberg |
| 5,477,851 A | 12/1995 | Callaghan |
| 5,499,625 A | 3/1996 | Frass |
| 5,499,970 A | 3/1996 | Olson |
| 5,562,608 A | 10/1996 | Sekins |
| 5,622,182 A | 4/1997 | Jaffe |
| 5,632,271 A | 5/1997 | Brain |
| 5,653,229 A | 8/1997 | Greenberg |
| 5,720,275 A | 2/1998 | Patil |
| 5,743,254 A | 4/1998 | Parker |
| 5,743,258 A | 4/1998 | Sato |
| 5,746,202 A | 5/1998 | Pagan |
| 5,771,889 A | 6/1998 | Pagan |
| 5,819,733 A | 10/1998 | Bertram |
| 5,853,004 A | 12/1998 | Goodman |
| 5,865,176 A | 2/1999 | O'Neil |
| 5,878,745 A | 3/1999 | Brain |
| 5,896,858 A | 4/1999 | Brain |
| 5,906,584 A | 5/1999 | Pavoni |
| 5,983,897 A | 11/1999 | Pagan |
| 6,001,077 A | 12/1999 | Ellman |
| 6,053,166 A | 4/2000 | Gomez |
| 6,119,695 A | 9/2000 | Augustine |
| 6,168,579 B1 | 1/2001 | Tsugita |
| 6,196,224 B1 | 3/2001 | Alfery |
| 6,256,524 B1 | 7/2001 | Walker |
| 6,321,749 B1 | 11/2001 | Toti |
| 6,386,199 B1 | 5/2002 | Alfery |
| 6,398,775 B1 | 6/2002 | Perkins |
| 6,520,183 B1 | 2/2003 | Amar |
| 6,526,977 B1 | 3/2003 | Gobel |
| 6,527,761 B1 | 3/2003 | Soltesz et al. |
| 6,550,475 B1 | 4/2003 | Oldfield |
| 6,626,169 B1 | 9/2003 | Gaitini |
| 6,659,961 B1 | 12/2003 | Robinson |
| 2001/0041861 A1 | 11/2001 | Gobel |
| 2002/0077593 A1 | 6/2002 | Perkins |
| 2002/0170556 A1 | 11/2002 | Gaitini |
| 2004/0020491 A1 | 2/2004 | Fortuna |

FOREIGN PATENT DOCUMENTS

| | | |
|---|---|---|
| GB | 1535060 | 12/1978 |
| JP | 10179745 A | 7/1998 |
| WO | WO 92/13587 | 8/1992 |
| WO | WO 98/18383 | 5/1998 |
| WO | WO 99/45991 | 9/1999 |

PERILARYNGEAL ORAL AIRWAY WITH MULTI-LUMEN ESOPHOGEAL-OBTURATOR

FIELD OF THE INVENTION

The present invention is directed to artificial airways, and more particularly to an artificial airway esophageal-obturator facilitating self or artificial ventilation of the lungs of a patient.

BACKGROUND OF THE INVENTION

Oral airways were introduced into the practice of anesthesia and cardiopulmonary resuscitation several decades ago. The primary purpose of oral airways is to help provide a patient airway that allows positive pressure to be applied by a practitioner. Artificial airway devices providing a combination of an airway and an esophageal-obturator are well known in the art. Among the patents teaching such devices are Fortuna, U.S. Patent Application Publication No. U.S. 2004/0020491 A1; O'Neil, U.S. Pat. No. 5,865,176; Bertram, U.S. Pat. No. 5,819,733; Brain, U.S. Pat. No. 5,632,271; Frass, U.S. Pat. No. 5,499,625; Sato, U.S. Pat. No. 5,392,774; Frass, U.S. Pat. No. 4,688,568; and Young, U.S. Pat. No. 4,230,108. The content of each of these patents is incorporated by reference herein.

Each of these patents are generally directed to the concept of isolating the oral airway from a patient's esophagus while providing an esophageal-obturator for allowing communication with the esophagus through a lumen distinct from that providing communication with the larynx. However, each of these devices suffers from one or more shortcomings including: difficulty of placement within a patient; complexity in manufacture and expensive components rendering the devices unnecessarily expensive; lack of reliability in properly seating the devices within a patient; limited access to the patient's esophagus; and difficulty in using the airway for inserting an endotracheal tube. Accordingly, the present invention is directed to overcoming one or more of these problems.

SUMMARY OF THE INVENTION

A first aspect of the invention is a tubular assembly including a plurality of lumens. The tubular assembly is configured for insertion into the mouth and throat of a patient with a proximal end of the tubular assembly extending from the patient's mouth and distal end of the tubular assembly extending into the patient's esophagus. The tubular assembly further includes a transition portion near the distal end of the tubular assembly. The transition portion is configured to transition from a relatively radially large proximal end to a relatively radially small distal end, with the relatively radially small distal end being in communication with at least one of the lumens. The relatively radially large proximal end is configured to abut the aryepiglottic folds of the patient to arrest insertion of the tubular assembly with the relatively radially small distal end of the transition portion extending into the patient's esophagus. The plurality of lumens may further comprise a laryngeal lumen having a distal end in the transition portion proximal of the relatively radially small distal end, the distal end of the laryngeal lumen being located in the transition portion so that the distal end of the laryngeal lumen is in fluid communication with the larynx of a patient with the relatively radially large proximal end of the transition portion abutting the aryepiglottic folds. The distal end of the laryngeal lumen may be covered by a plurality of bars. The tubular assembly may further include a first inflatable cuff near the relatively radially small distal end of the transition portion configured for insertion into the esophagus of a patient with a relatively radially large proximal end of the transition portion abutting the aryepiglottic folds of the patient and a second inflatable cuff proximal the first inflatable cuff configured to reside in the patient's hypopharynx with the relatively radially large proximal end of the transition portion abutting the aryepiglottic folds. Inflation lumens are preferably provided and extend between each of the first and second inflatable cuffs and near the proximal end of the tubular assembly. The first and second cuffs are preferably configured to form a seal with a wall of the esophagus and the hypopharynx, respectively, when inflated to so as to enable flow of pressurized gas through the laryngeal lumen and into the larynx. Preferably two lumens are provided in fluid communication with the relatively radially small distal end of the transition portion and the two lumens are positioned proximal the relatively radially large proximal end of the transition portion with the laryngeal lumen sandwiched between the two lumens. The two lumens preferably communicate with a manifold within the relatively radially small distal end of the transitional portion. Preferably, the tubular assembly comprises a proximal portion comprising the two lumens and the laryngeal lumen proximal the relatively radially large proximal end of the transition portion and a housing defining the transition portion. The housing is configured to receive a proximal portion of a relatively large effective diameter, transition to the distal portion of the relatively small effective diameter and to define the distal end of the laryngeal lumen. Preferably the housing comprises a ramp within the laryngeal lumen near the distal end of the laryngeal opening, the ramp being configured to guide an endotracheal tube axially inserted into the proximal end of the laryngeal lumen out the distal opening of the laryngeal lumen. The ramp may comprise a plurality of fins extending lengthwise of the housing.

A second aspect of the invention is a tubular assembly comprising a plurality of lumens, the tubular assembly being configured for insertion into the mouth and throat of a patient with a proximal end of the tubular assembly extending from the patient's mouth and a distal end of the tubular assembly extending into the patient's esophagus. At least two of the plurality of lumens is in fluid communication with an opening at the distal end of the tubular assembly for fluid communication with the patient's esophagus and at least one of the plurality of lumens defines a laryngeal lumen having an opening configured for fluid communication with the patient's larynx with the distal end extending into the patient's esophagus. A first cuff may be operatively associated with the tubular assembly near the distal end to seat in the patient's esophagus with the distal end in the patient's esophagus. A second cuff operatively associated with the tubular assembly is proximal of the opening of the laryngeal lumen and configured to reside in the patient's hypopharynx with the distal end in the patient's esophagus. The first and second cuffs are preferably configured to form a seal with a wall of the esophagus and the hypopharynx, respectively, when inflated so as to enable a flow of pressurized gas through the laryngeal lumen and into the larynx.

A third aspect of the present invention is a method of providing breathing assistance to a patient including providing a tubular assembly comprising a plurality of lumens and a transitional portion near a distal end of the tubular assembly. The transition portion is configured to transition from a relatively radially large proximal end to a relatively radially small distal end, the relatively radially small distal end being in communication with at least one of the lumens and the relatively radially large proximal end being sized to prevent its insertion into the esophagus of a patient. The method further includes inserting the distal end of the assembly into the mouth and throat of a patient and abutting the aryepiglottic folds of a patient with the relatively radially large proximal end to arrest insertion of the tubular assembly into a patient with the relatively radially small distal end of the transition portion extending into the patient's esophagus. The tubular assembly may further include a laryngeal lumen terminating at an opening in the transition portion. The method may then further include aligning the opening adjacent to a larynx of a patient. The tubular assembly preferably further comprises a first inflatable cuff near the relatively radially small distal end of the transition portion and a second inflatable cuff near the proximal end of the transitional portion, the first inflatable cuff being inserted into the esophagus and the second inflatable cuff residing in the patient's hypopharynx with the relatively radially large proximal end abutting the aryepiglottic folds. The method then further includes inflating the first and second inflatable cuffs. The method may further include connecting a proximal end of the laryngeal lumen in fluid communication with a ventilator. The method may further include axially inserting an endotracheal tube into the laryngeal lumen and directing the endotracheal tube into the larynx of a patient.

The apparatus and method of the present invention provide an apparatus for providing breathing support while enabling access to the esophagus for monitoring parameters such as temperature or removal of gastric fluids. The method and apparatus further provide for isolation of the patient's larynx to minimize the risk of aspirating the contents of the esophagus or stomach. These advantages are provided by a device that can be manufactured in a cost effective manner and can be quickly and accurately operatively inserted into a patient's throat to insure safe and effective manual or assisted ventilation.

DETAILED DESCRIPTION OF THE PREFERRED EMBODIMENT

Figure 2:
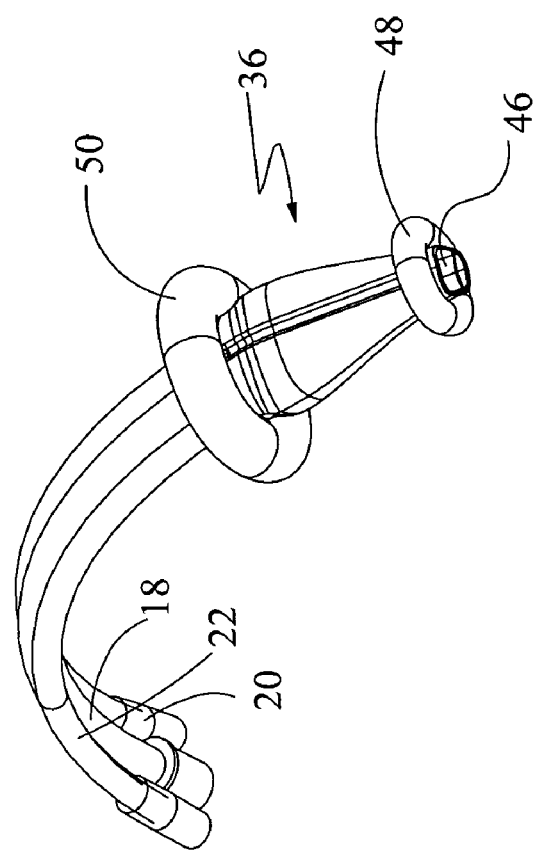
FIG. 2 is a posterior perspective view of the apparatus of FIG. 1.
Figure 1:
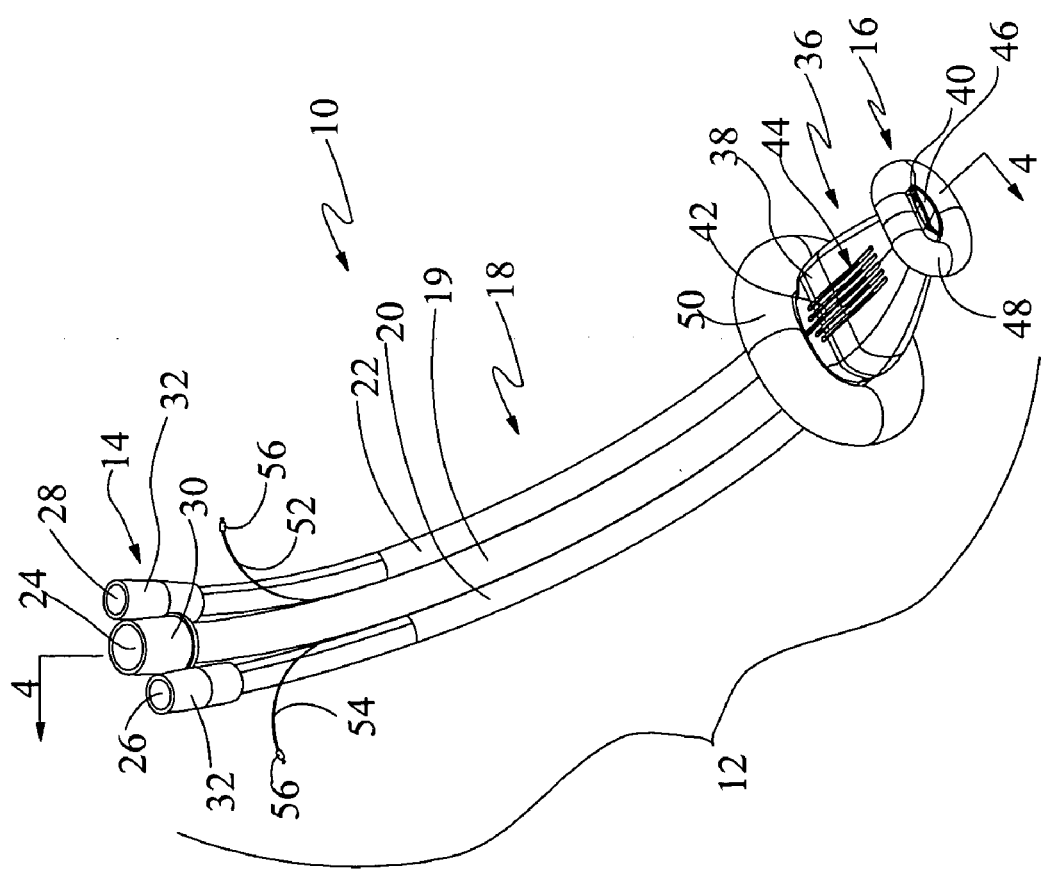
FIG. 1 is a perspective anterior view of an apparatus for providing breathing assist in accordance with the present invention.

An apparatus 10 for providing breathing assist, more particularly a perilaryngeal oral airway with multi-lumen esophageal-obturator, is shown in an anterior perspective view in FIG. 1. The apparatus consists of a tubular assembly 12 having a proximal end 14 and a distal end 16. As seen in FIG. 1 and FIG. 2 (a posterior perspective view of the apparatus), the tubular assembly 12 has an anterior radius to aid in conforming the tubular assembly 12 to the mouth and throat of a patient during insertion therein, as will be discussed in greater detail below.

The tubular assembly 12 includes a plurality of tubes 18 including a laryngeal tube 19 and first and second tubes 20, 22 which define a laryngeal lumen 24 and first and second lumens 26, 28, respectively. The tubes are juxtaposed with the first and second tubes 20, 22 sandwiching the laryngeal tube 19 and the tubes attached lengthwise. The laryngeal tube 19 includes an adaptor 30 attached to its proximal end to allow for connection to a respiratory circuit or anesthesia circuit (not shown) as conditions may require. Likewise, connectors 32 are provided on the proximal ends of the first and second tubes 20, 22 to allow for connection to suction devices or to simply facilitate insertion of instruments such as temperature probes within the first and second lumens 26, 28.

Each of the plurality of tubes 18 is preferably formed of a material such as polyvinylchloride or other thermoplastic that is relatively axially rigid yet radially flexible so that when inserted into the mouth, oral cavity and pharynx of a patient, it may follow the anatomical contours. The anterior radius best seen in FIGS. 1 and 2 further assists insertion. The material is also preferably sufficiently flexible so that a surgeon operating on the oral cavity or pharynx with the apparatus for providing breathing assist in place can deflect the tubular member out of the operating field. Each of the tubes further are preferably radially robust to not kink during insertion or manipulation. Although not shown, each of the tubes 19, 20 and 22 may include wire reinforcing wound into its wall. The tubes are attached lengthwise by, for example, heat staking or adhesive bonding.

The tubular assembly 12 further includes a housing 36 is attached to the distal end of the laryngeal tube 19 and first and second tubes 20, 22. The housing 36 constitutes a transition portion of the tubular assembly 12 which transitions the tubular assembly from a relatively radially large proximal end 38 to a relatively radially small distal end 40. A plurality of bars 42 cover a distal opening 44 of the laryngeal lumen 24 in an anterior surface of the housing 36. An esophageal opening 46 is defined at the termination of the relatively radially small distal end and the esophageal opening 46 is in fluid communication with each of the first and second lumens 26, 28. A first inflatable cuff 48 is attached to the housing 36 near the relatively radially small distal end 40 and a second inflatable cuff 50 is located on the tubular assembly proximal of the distal opening of the laryngeal lumen 44. Each of the first and second inflatable cuffs 48, 50 are in fluid communication with inflation lumens 52, 54, each of which have a self-sealing valve 56 on its proximal end which extends near the proximal end of the tubular assembly 12.

Figure 3:
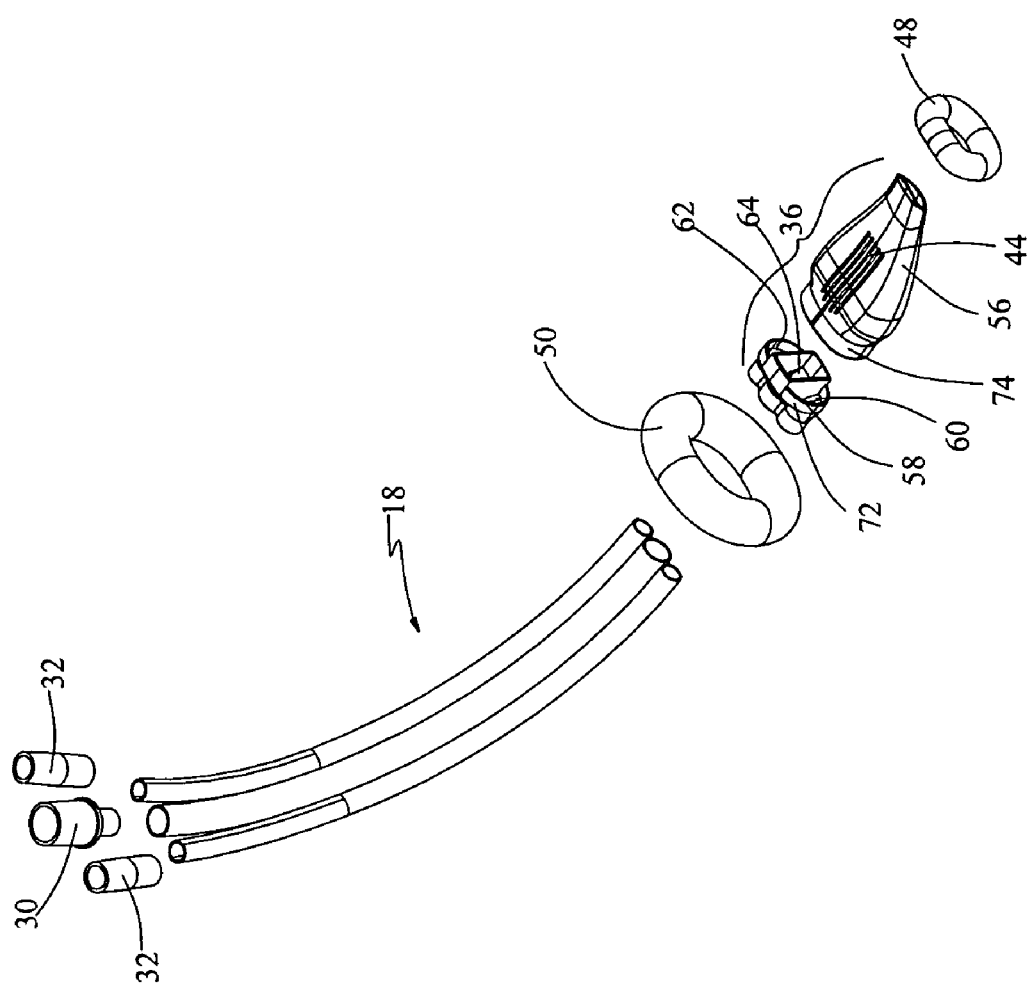
FIG. 3 is an exploded view of the apparatus of FIG. 1.
Figure 4:
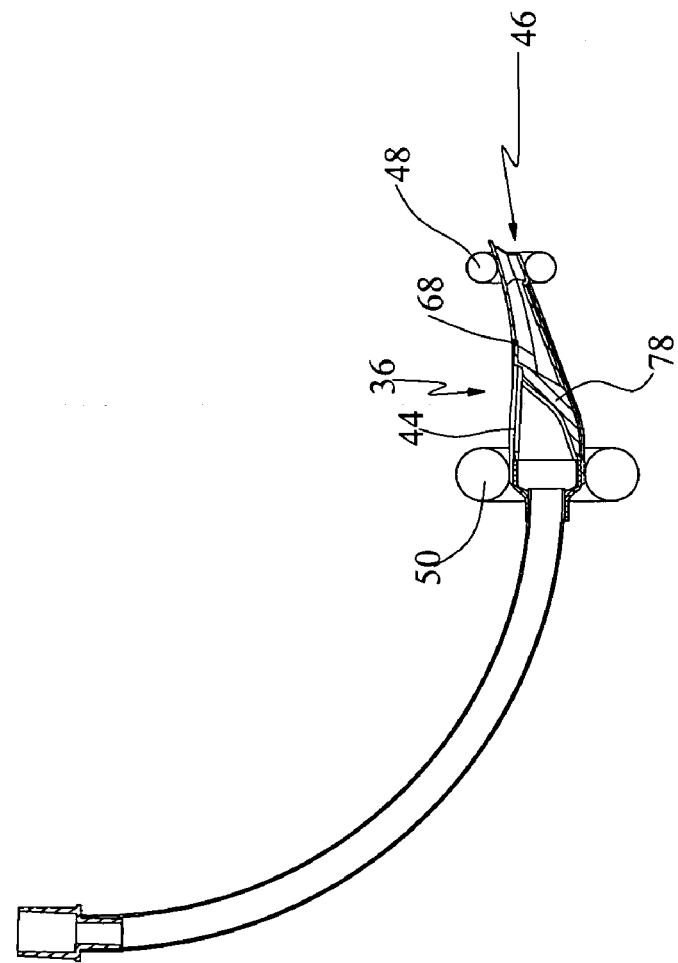
FIG. 4 is a cross-sectional view of the apparatus of FIG. 1 view taken along line 4—4 of FIG. 1.

FIG. 3 is an exploded view of the apparatus for providing breathing assist of FIGS. 1 and 2 and like reference numbers are used with like elements of FIG. 3. The housing 36 consists of a main body 56 and an adaptor 58. The adaptor 58 is configured to receive the distal ends of the plurality of tubes 18 for attachment to the housing 36. The adaptor 58 has first and second chambers 60, 62 corresponding to and forming part of the first and second lumens 26, 28 and a laryngeal chamber 64 corresponding to and forming part of the laryngeal lumen 24. The laryngeal chamber 64 transitions the laryngeal lumen 24 into fluid communication with the distal opening of the laryngeal lumen 24. The first and second chambers 60, 62 in turn are in communication with lumen segments within the housing 56 that enable the first and second lumens to be in fluid communication with a manifold 68 within the housing which in turn is in fluid communication with the esophageal opening 46, as best seen in FIG. 4. The distal end of the adaptor 58 defines a circumferential lip 72 configured to be received within a receiving flange 74 of the main body 56, as best viewed in FIG. 4.

FIG. 4, which is a cross-section of the apparatus of FIG. 1, illustrates the interior of the housing 36. Within the housing the laryngeal lumen includes a plurality of lengthwise oriented fins 78 that define a ramp terminating at the distal opening 44 of the laryngeal lumen. As will be described in greater detail with reference to FIG. 9, the ramp defined by the lengthwise oriented fins 78 is configured to direct an endotracheal tube into the larynx of a patient with the apparatus operative inserted within a patient. Manufacturing the housing using the plurality of fins helps to maintain a substantially uniform material thickness throughout the housing which enhances manufacturability of the housing. The housing is made of a material that is relatively flexible and soft so that there is some give as the housing is inserted into the patient. The particular firmness of the housing must strike a balance between the need to hold the hypo-pharyngeal and perilaryngeal structures away from the opening, the need to move soft tonsil and oral-pharyngeal tissue to the side as the oral airway is inserted and the desire for the oral airway to be able to bend inward when inserted through the back of a patient's mouth. To help achieve this balance, the housing is preferably made of a non-toxic polyvinylchloride having a durometer of about 80 Shore A or less.

Each of the various components of the tubular assembly 12 are attached by adhesives, thermal bonding or the like.

Figure 5:
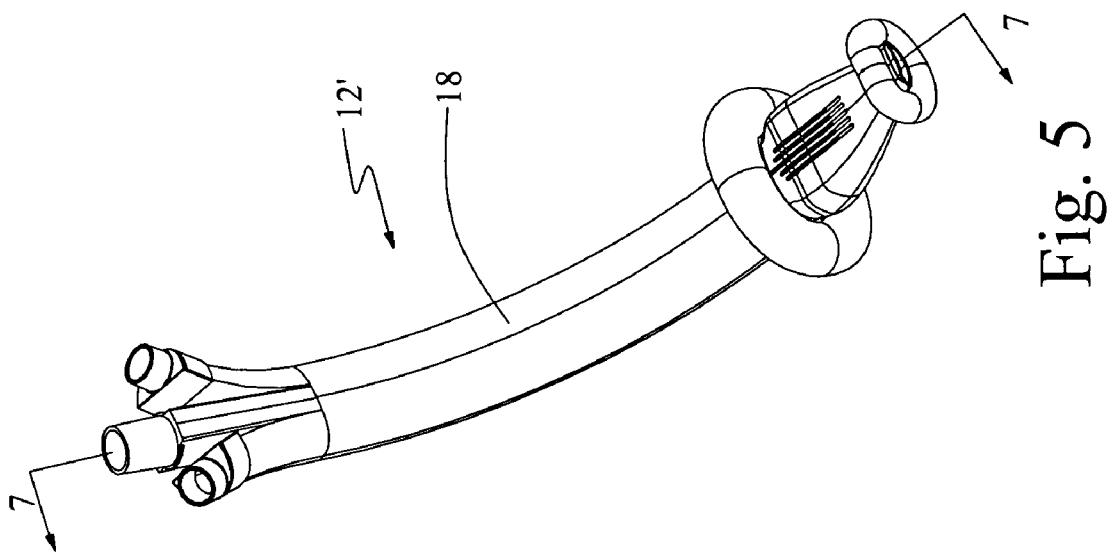
FIG. 5 is an anterior perspective view of an alternate embodiment of a apparatus for providing breathing assist.
Figure 7:
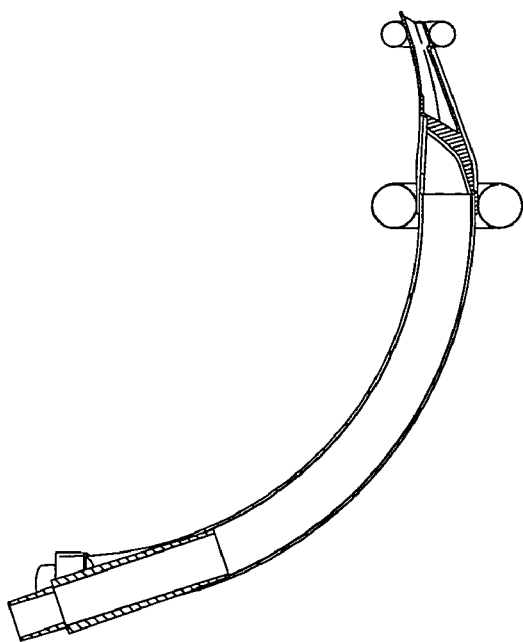
FIG. 7 is a cross-sectional view of the apparatus of FIG. 5 taken along line 7—7 of FIG. 5.
Figure 6:
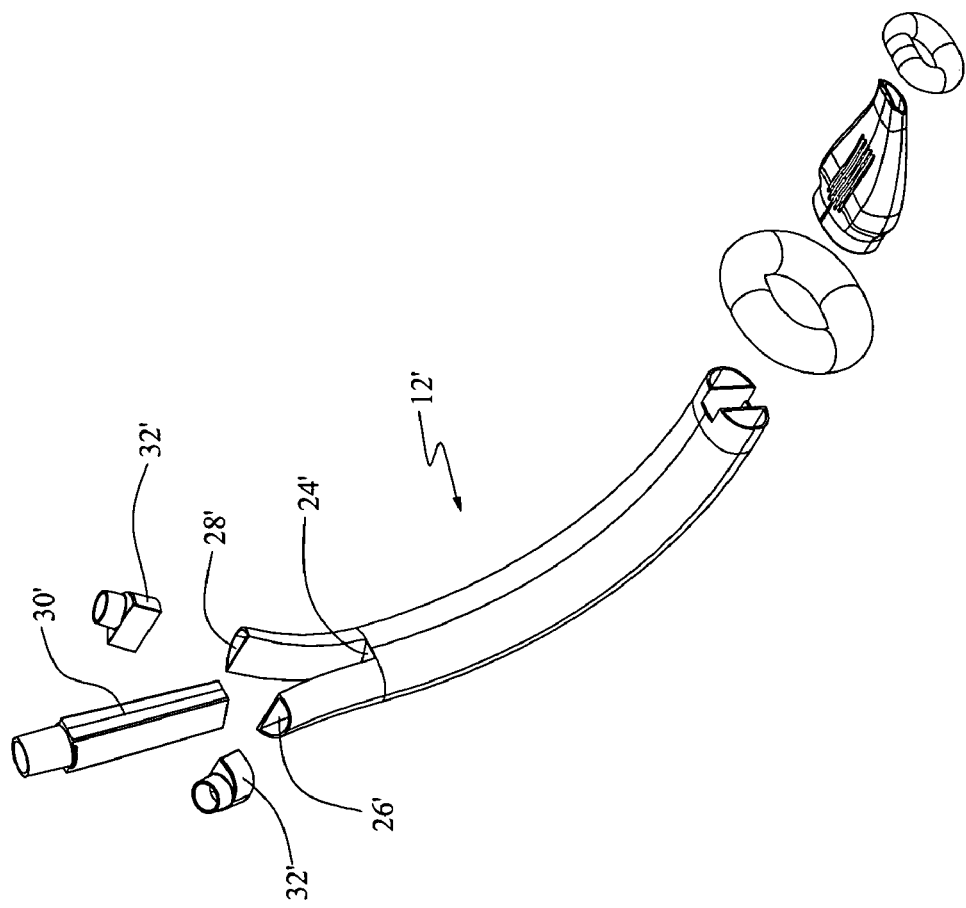
FIG. 6 is an exploded view of the apparatus of FIG. 5.

FIGS. 5 and 6 are an alternative embodiment of the tubular assembly 12. Identical elements will have identical reference numbers followed by a prime (') when describing FIGS. 5-7. The tubular assembly 12' is identical in all respects except for the structure of the plurality of tubes 18'. Rather than having distinct tubes that are attached by heat staking, adhesive or the like, the tubular assembly 12' illustrated in FIG. 5 has the laryngeal tube 19, first tube 20 and second tube 22 integrally formed as a single unit 18'. For example, the tubes 19, 20 and 22 may be extruded. Referring to FIG. 6, substantially identical connectors 32' are provided for each of the first and second lumens 26', 28' and an elongated adaptor 30' is provided for the laryngeal lumen 24. In all other material respects the second embodiment of the tubular assembly 12' is identical to the first embodiment of the tubular assembly 12 discussed above.

Figure 9:
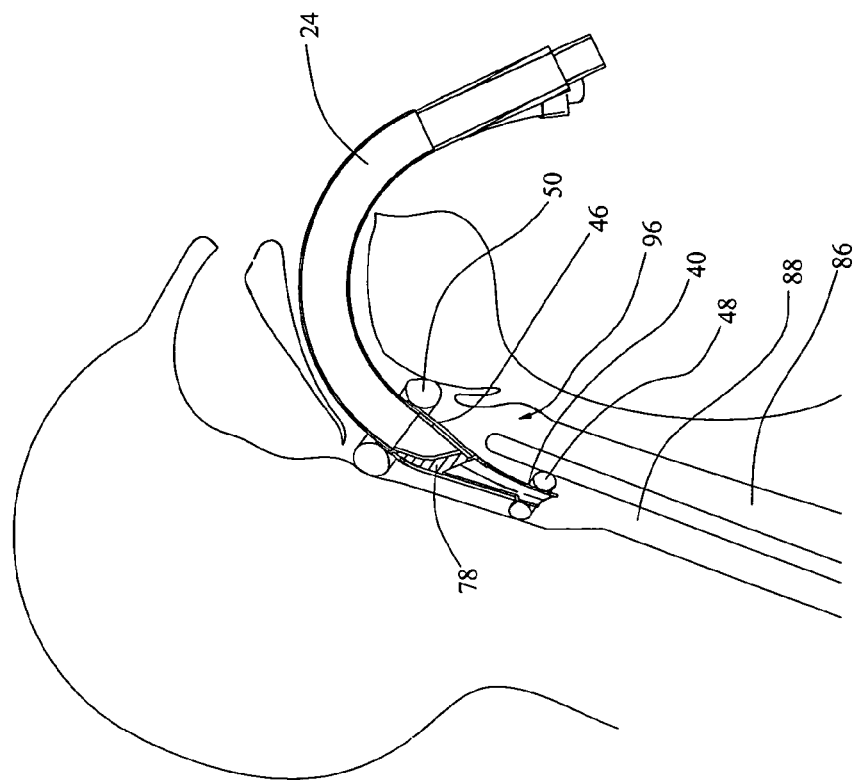
FIG. 9 illustrates the apparatus of FIG. 5 operatively seated in the throat of a patient.
Figure 8:
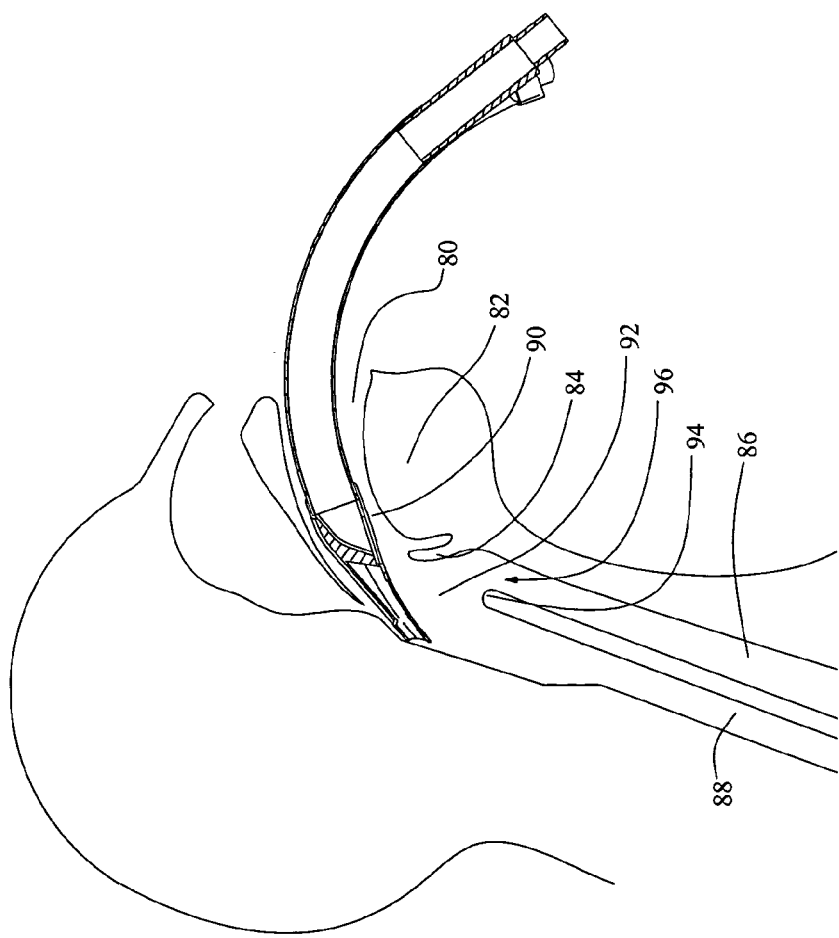
FIG. 8 illustrates the insertion of the apparatus of FIG. 5 into the throat of a patient.

FIGS. 8 and 9 illustrate insertion and seating of the apparatus 10 for providing breathing assist within a patient. FIGS. 8 and 9 each include simplified anatomical illustration of a patient's head, including the oral airway defined by the oral cavity 80, the tongue 82, the epiglottis 84, the trachea 86, the esophagus 88, the pharynx 90, the hypopharynx 92, the arytenoid cartilage 94 and the glottis or larynx generally indicated at 96. The various cartilage, muscular tissue and vocal chords comprising the glottis or larynx have been eliminated for the sake of clarity.

In use, the apparatus for providing breathing assist is inserted with the housing leading into the mouth or oral cavity 80 of a patient. The distal end of the housing 36 guides the tubular assembly over the tongue 82 and as the distal end 16 of the housing 36 abuts the posterior wall of the pharynx 90 the housing flexes toward the distal opening of the laryngeal lumen 44 causing the bars 42 to deflect laterally as the housing flexes, thus enhancing the flexibility of the housing. The flexing of the housing as described above effectively shortens the length of the housing, making it easier for the housing to make the bend into the hypopharynx. Upon further insertion of the apparatus 10 for providing breathing assist into the throat of a patient, the housing rebounds to its original shape and the flexible bars encounter the epiglottis 84 and the epiglottis rides up the flexible bars. Axial insertion of the housing is intended to be arrested by the relatively radially large proximal end 38, more particularly, side walls of the relatively radially large proximal end 38, coming into abutment with the aryepiglottic folds within the hypopharynx 92. As illustrated in FIG. 9, with the tubular assembly 12 properly seated, the relatively radially small distal end 40 of the housing 36 is seated in the esophagus 88 and the esophageal opening 46 in the anterior side of the housing is substantially aligned with the larynx 96. The first and second inflatable cuffs 48, 50 are then preferably inflated with the first cuff 48 substantially forming a seal with the esophagus 88 and the second inflatable cuff 50 substantially forming a seal with the pharynx 90. "Substantially forming a seal" means, with respect to the first cuff, preventing harmful amounts of stomach or esophageal fluids from refluxing into the patient's larynx and with respect to the second cuff, facilitating pressurized breathing assist. When thus installed within a patient, pressurized breathing assist can be provided to the patient via the laryngeal lumen. The cuffs in addition to the structure of the housing maintain all the soft tissue surrounding the hypopharynx and the larynx back from the opening 46 and an unobstructed airway is provided to the trachea 84 for assisted or unassisted patient breathing. With further reference to FIG. 9, in the event a clinician determines an endotracheal tube is to be installed in the trachea of a patient, the endotracheal tube can be advanced through the laryngeal lumen 24 and into the esophagus 86 by virtue of the thin lengthwise oriented fins 78 which define a guiding ramp. The flexible bars 42 are flexible enough so that the endotracheal tube or instrument can be inserted into a gap between adjacent bars to deform the bars laterally. To aid in passing an instrument through the bars, the bars may be formed with lengthwise posterior facing apexes, have a circular cross-section or a flat posterior surface may be adequate.

What is claimed is:

1. An apparatus comprising:
    a tubular assembly comprising a plurality of lumens, the tubular assembly being configured for insertion into the mouth and throat of a patient with a proximal end of the tubular assembly extending from the patient's mouth and a distal end of the tubular assembly extending into the patient's esophagus, the tubular assembly further comprising a transition portion near the distal end of the tubular assembly, the transition portion comprising an outer wall defining at least in part a chamber corresponding to each lumen, the outer wall of the transition portion being configured to transition from a relatively radially large proximal end to a relatively radially small distal end, the relatively radially small distal end being in communication with at least one of the lumens, the relatively radially large proximal end being configured to abut the aryepiglottic folds of the patient to arrest insertion of the tubular assembly with the relatively radially small distal end of the transition portion extending into the patient's esophagus.

2. The apparatus of claim 1 wherein the plurality of lumens further comprises a laryngeal lumen, the laryngeal lumen having a distal end opening in the transitional portion proximal of the relatively radially small distal end, the distal end opening of the laryngeal lumen being located relative to the transition portion so that the distal end opening of the laryngeal lumen is in fluid communication with a larynx of a patient with the relatively radially large proximal end of the transition portion abutting the aryepiglottic folds.

3. The apparatus of claim 2 wherein the distal end opening of the laryngeal lumen is covered by a plurality of bars.

4. The apparatus of claim 2 further comprising a first inflatable cuff near the relatively radially small distal end of the transitional portion configured for insertion into the esophagus of a patient with the relatively radially large proximal end of the transition portion abutting the aryepiglottic folds of the patent and a second inflatable cuff proximal the first inflatable cuff configured to reside in the patient's hypo-pharynx with the relatively radially large proximal end of the transition portion abutting the aryepiglottic folds.

5. The apparatus of claim 4 further comprising an inflation lumen extending between each of the first and second inflatable cuffs and near the proximal end of the tubular assembly.

6. The apparatus of claim 4 wherein the first and second cuffs are configured to form a seal with a wall of the esophagus and the hypo-pharynx, respectively, when inflated so as to enable flow of pressurized gas through the laryngeal lumen and into the larynx.

7. The apparatus of claim 2 further comprising two lumens in fluid communication with the relatively radially small distal end of the transition portion and the two lumens and the laryngeal lumen being juxtaposed proximal the relatively radially large proximal end of the transition portion with the laryngeal lumen being sandwiched by the two lumens.

8. The apparatus of claim 7 wherein the two lumens communicate with a manifold within the relatively radially small distal end of the transition portion.

9. The apparatus of claim 8 wherein the tubular assembly comprises a proximal portion comprising the two lumens and the laryngeal lumen proximal the relatively radially large proximal end of the transition portion and a housing defining the transition portion, the housing being configured to receive the proximal portion of a relatively large effective diameter, transition to the distal portion of a relatively small effective diameter and to define the distal end of the laryngeal lumen.

10. The apparatus of claim 9 wherein the housing comprises a ramp within the laryngeal lumen near the distal end of the laryngeal opening, the ramp being configured to guide an endotracheal tube axially inserted into the proximal end of the laryngeal lumen out the distal opening of the laryngeal lumen.

11. The apparatus of claim 10 wherein the ramp comprises a plurality of fins extending lengthwise of the housing.

12. An apparatus comprising:
a tubular assembly comprising a plurality of lumens, the tubular assembly being configured for insertion into the mouth and throat of a patient with a proximal end of the tubular assembly extending from the patient's mouth and a distal end of the tubular assembly extending into the patient's esophagus, at least two of the plurality of lumens being in fluid communication with an opening at the distal end of the tubular assembly for fluid communication with the patient's esophagus and at least one of the plurality of lumens defining a laryngeal lumen having an opening configured for fluid communication with the patient's larynx with the distal end extending into the patient's esophagus.

13. The apparatus of claim 12 further comprising:
a first cuff operatively associated with the tubular assembly near the distal end to seat in the patient's esophagus with the distal end in the patient's esophagus and a second cuff operatively associated with the tubular assembly proximal of the opening of the laryngeal lumen configured to reside in the patient's hypo-pharynx with the distal end in the patient's esophagus.

14. The apparatus of claim 13 wherein the first and second cuffs are configured to form a seal with a wall of the esophagus and the hypo-pharynx, respectively, when inflated so as to enable flow of pressurized gas through the laryngeal lumen and into the larynx.

15. A method of providing breathing assistance to a patient comprising:
providing a tubular assembly comprising a plurality of lumens and a transition portion near a distal end of the tubular assembly, the transition portion comprising an outer wall defining at least in part a chamber corresponding to each lumen, the outer wall of the transition portion being configured to transition from a relatively radially large proximal end to a relatively radially small distal end, the relatively radially small distal end being in communication with at least one of the lumens, the relatively radially large proximal end being sized to prevent its insertion into the esophagus of a patient;
inserting the distal end of the tubular assembly into the mouth and throat of a patient; and
abutting aryepiglottic folds of a patient with the relatively radially large proximal end to arrest insertion of the tubular assembly into a patient with the relatively radially small distal end of the transition portion extending a select distance into the patient's esophagus.

16. The method of claim 15 wherein the tubular assembly further comprises a laryngeal lumen terminating at an opening in the transition portion, the method further comprising:
aligning the opening adjacent to a larynx of the patient.

17. The method of claim 16 wherein the tubular assembly further comprises a first inflatable cuff near the relatively radially small distal end of the transition portion and a second inflatable cuff near the proximal end of the transition portion, the first inflatable cuff being inserted in the esophagus and the second inflatable cuff residing in the patients hypo-pharynx with the relatively radially large proximal end abutting the aryepiglottic folds, the method further comprising:
inflating the first and second inflatable cuffs.

18. The method of claim 17 further comprising connecting a proximal end of the laryngeal lumen in fluid communication with a ventilator.

19. The method of claim 16 further comprising:
axially inserting an endotracheal tube into the laryngeal lumen; and
directing the endotracheal tube into the larynx of a patient.

* * * * *